US006805853B2

(12) United States Patent
Rabinowitz et al.

(10) Patent No.: US 6,805,853 B2
(45) Date of Patent: Oct. 19, 2004

(54) DELIVERY OF DIAZEPAM THROUGH AN INHALATION ROUTE

(75) Inventors: Joshua D. Rabinowitz, Mountain View, CA (US); Alejandro C. Zaffaroni, Atherton, CA (US)

(73) Assignee: Alexza Molecular Delivery Corporation, Palo Alto, CA (US)

( * ) Notice: Subject to any disclaimer, the term of this patent is extended or adjusted under 35 U.S.C. 154(b) by 0 days.

(21) Appl. No.: 10/150,056

(22) Filed: May 15, 2002

(65) Prior Publication Data

US 2003/0091511 A1 May 15, 2003

Related U.S. Application Data

(60) Provisional application No. 60/345,882, filed on Nov. 9, 2001.

(51) Int. Cl.[7] .................................................. A61K 9/12
(52) U.S. Cl. .......................... 424/45; 424/46; 514/220; 128/200.24; 128/204.18
(58) Field of Search ..................... 424/45, 46; 514/220; 128/200.24, 204.18

(56) References Cited

U.S. PATENT DOCUMENTS

| | | | |
|---|---|---|---|
| RE30,285 E | 5/1980 | Babington | |
| 4,229,447 A | 10/1980 | Porter | |
| 4,863,720 A | 9/1989 | Burghart et al. | |
| 5,099,861 A | 3/1992 | Clearman et al. | |
| 5,388,574 A | 2/1995 | Ingebrethsen | |
| 5,457,100 A | 10/1995 | Daniel | |
| 5,543,434 A | 8/1996 | Weg | |
| 5,544,646 A | 8/1996 | Lloyd et al. | |
| 5,655,523 A | 8/1997 | Hodson et al. | |
| 5,694,919 A | 12/1997 | Rubsamen et al. | |
| 5,735,263 A | 4/1998 | Rubsamen et al. | |
| 5,758,637 A | 6/1998 | Ivri et al. | |
| 5,767,117 A | 6/1998 | Moskowitz | |
| 5,915,378 A | 6/1999 | Lloyd et al. | |
| 5,934,272 A | 8/1999 | Lloyd et al. | |
| 5,957,124 A | 9/1999 | Lloyd et al. | |
| 5,960,792 A | 10/1999 | Lloyd et al. | |
| 5,985,309 A | 11/1999 | Edwards et al. | |
| 6,041,777 A * | 3/2000 | Faithfull et al. ....... | 128/200.24 |
| 6,048,857 A | 4/2000 | Ellinwood, Jr. et al. | |
| RE36,744 E | 6/2000 | Goldberg | |
| 6,095,153 A | 8/2000 | Kessler et al. | |
| 6,102,036 A | 8/2000 | Slutsky et al. | |
| 6,140,323 A | 10/2000 | Ellinwood, Jr. et al. | |
| 6,514,482 B1 * | 2/2003 | Bartus et al. ............ | 424/45 |
| 6,591,839 B2 | 7/2003 | Meyer et al. | |
| 2002/0058009 A1 | 5/2002 | Bartus et al. | |
| 2003/0032638 A1 | 2/2003 | Kim et al. | |

FOREIGN PATENT DOCUMENTS

| | | |
|---|---|---|
| CA | 2152684 | 1/1996 |
| EP | 0 358 114 | 3/1990 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 98/22170 | 5/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |

OTHER PUBLICATIONS

Office Action mailed Aug. 13, 2003 for U.S. application 10/153,313 filed May 21, 2002 "Delivery of Benzodiazepines Through an Inhalation Route".

Bennett, R.L. et al. (1981). "Patient–Controlled Analgesia: A New Concept of Postoperative Pain Relief," *Annual Surg.* 195(6):700–705.

Carroll, M.E. et al. (1990), "Cocaine–base smoking in rhesus monkeys: reinforcing and physiological effects," *Psychopharmacology* (Berl). 102:443–450.

Clark, A. and Byron, P. (1986). "Dependence of Pulmonary Absorption Kinetics on Aerosol Particle Size," *Z. Erkrank.* 166:13–24.

Darquenne, C. et al. (1997). "Aerosol Dispersion in Human Lung: Comparison Between Numerical Simulations and Experiments for Bolus Tests," *American Physiological Society.* 966–974.

(List continued on next page.)

*Primary Examiner*—Michael G. Hartley
*Assistant Examiner*—Mina Haghighatian
(74) *Attorney, Agent, or Firm*—Elaine C. Stracker

(57) ABSTRACT

The present invention relates to the delivery of diazepam through an inhalation route. Specifically, it relates to aerosols containing diazepam that are used in inhalation therapy. In a composition aspect of the present invention, the aerosol comprises particles comprising at least 5 percent by weight of diazepam. In a method aspect of the present invention, diazepam is delivered to a mammal through an inhalation route. The method comprises: a) heating a composition, wherein the composition comprises at least 5 percent by weight of diazepam, to form a vapor; and, b) allowing the vapor to cool, thereby forming a condensation aerosol comprising particles, which is inhaled by the mammal. In a kit aspect of the present invention, a kit for delivering diazepam through an inhalation route to a mammal is provided which comprises: a) a composition comprising at least 5 percent by weight of diazepam; and, b) a device that forms a diazepam containing aerosol from the composition, for inhalation by the mammal.

15 Claims, 1 Drawing Sheet

OTHER PUBLICATIONS

Davies, C.N. et al. (May 1972). "Breathing of Half–Micron Aerosols," *Journal of Applied Physiology.* 32(5):591–600.

Dershwitz, M., M.D., et al. (Sep. 2000). "Pharmacokinetics and Pharmacodynamics of Inhaled versus Intravenous Morphine in Healthy Volunteers," *Anesthesiology.* 93(3): 619–628.

Finlay, W.H. (2001). "The Mechanics of Inhaled Pharmaceutical Aerosols", Academic Press: San Diego Formula 2.39. pp. 3–14 (Table of Contents). pp. v–viii.

Gonda,I. (1991). "Particle Deposition in the Human Respiratory Tract," Chapter 176, *The Lung: Scientific Foundations.* Crystal R.G. and West, J.B. (eds.), Raven Publishers, New York. pp. 2289–2294.

Hatsukami D, et al. (May 1990) "A method for delivery of precise doses of smoked cocaine–base to humans." *Pharmacology Biochemistry & Behavior.* 36(1):1–7.

Heyder, J. et al. (1986). "Deposition of Particles in the Human Respiratory Tract in the Size Range 0.005–15 $\mu$m," *J. Aerosol Sci.* 17(5):811–822.

Huizer, H., "Analytical studies on illicit heron. V. Efficacy of volatilization during heroin smoking." *Pharmaceutisch Weekblad Scientific Edition* (1987). 9(4):203–211.

Hurt, R.D., MD and Robertson, C.R., PhD, (Oct. 1998). "Prying Open the Door to the Tobacco Industry's Secrets About Nicotine: The Minnesota Tobacco Trial," *JAMA* 280(13):1173–1181.

Lichtman, A.H. et al. (1996). "Inhalation Exposure to Volatilized Opioids Produces Antinociception in Mice," Journal of Pharmacology and Experimental Therapeutics. 279(1):69–76.

Martin, B.R. and Lue, L.P. (May/Jun. 1989). "Pyrolysis and Volatilization of Cocaine," *Journal of Analytical Toxicology* 13:158–162.

Mattox, A.J. and Carroll, M.E., (1996). "Smoked heroin self–administration in rhesus monkeys," *Psychopharmacology*, 125:195–201.

Meng, Y. et al. Inhalation Studies With Drugs of Abuse, *NIDA Research Monograph*, (1997) 173:201–224.

Meng, Y., et al. (1999). "Pharmacological effects of methamphetamine and other stimulants via inhalation exposure," *Drug and Alcohol Dependence.* 53:111–120.

Pankow, J.F. et al. (1997). "Conversion of Nicotine in Tobacco Smoke to Its Volatile and Available Free–Base Form Through the Action of Gaseous Ammonia," *Envron. Sci. Technol.* 31:2428–2433.

Pankow, J. (Mar. 2000). ACS Conference–San Francisco–Mar. 26, 2000. Chemistry of Tobacco Smoke. pp. 1–8.

Seeman, J. et al. (1999). "The Form of Nicotine in Tobacco. Thermal Transfer of Nicotine and Nicotine Acid Salts to Nicotine in the Gas Phase," *J. Agric. Food Chem.* 47(12):5133–5145.

Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271–1280.

Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," *Clinical Pharmacology & Therapeutics* 62(6):596–609.

Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior.* 55(2):237–248.

\* cited by examiner

DELIVERY OF DIAZEPAM THROUGH AN INHALATION ROUTE

This application claims priority to U.S. provisional application Ser. No. 60/345,882 entitled "Delivery of Diazepam Through an Inhalation Route," filed Nov. 9, 2001, Rabinowitz, the entire disclosure of which is hereby incorporated by reference.

FIELD OF THE INVENTION

The present invention relates to the delivery of diazepam through an inhalation route. Specifically, it relates to aerosols containing diazepam that are used in inhalation therapy.

BACKGROUND OF THE INVENTION

VALIUM® is a composition currently marketed for the management of anxiety disorders and the relief of anxiety symptoms. It is administered both orally and by injection. The active ingredient in VALIUM® is diazepam, which is typically provided in doses of 2 mg to 20 mg.

The delivery methods for diazepam have a number of limitations. Oral administration typically provides for a relatively long onset of action (e.g. $\geq 1$ h). Intravenous injection, while rapidly delivering a drug, involves the discomfort and risk of infection associated with catheterization or injection. It is desirable to provide a new route of administration for diazepam that allows for a rapid onset of action without the disadvantages of catheterization or injection. The provision of such a route is an object of the present invention.

SUMMARY OF THE INVENTION

The present invention relates to the delivery of diazepam through an inhalation route. Specifically, it relates to aerosols containing diazepam that are used in inhalation therapy.

In a composition aspect of the present invention, the aerosol comprises particles comprising at least 5 percent by weight of diazepam. Preferably, the particles comprise at least 10 percent by weight of diazepam. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of diazepam.

Typically, the aerosol has a mass of at least 10 µg. Preferably, the aerosol has a mass of at least 100 µg. More preferably, the aerosol has a mass of at least 200µ.

Typically, the aerosol particles comprise less than 10 percent by weight of diazepam degradation products. Preferably, the particles comprise less than 5 percent by weight of diazepam degradation products. More preferably, the particles comprise less than 2.5, 1, 0.5, 0.1 or 0.03 percent by weight of diazepam degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of Typically, the aerosol has an inhalable aerosol drug mass density of between 0.1 mg/L and 15 mg/L. Preferably, the aerosol has an inhalable aerosol drug mass density of between 0.2 mg/L and 10 mg/L. More preferably, the aerosol has an inhalable aerosol drug mass density of between 0.5 mg/L and 8 mg/L.

Typically, the aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the aerosol is formed by heating a composition containing diazepam to form a vapor and subsequently allowing the vapor to condense into an aerosol.

In a method aspect of the present invention, diazepam is delivered to a mammal through an inhalation route. The method comprises: a) heating a composition, wherein the composition comprises at least 5 percent by weight of diazepam; and, b) allowing the vapor to cool, thereby forming a condensation aerosol comprising particles, which is inhaled by the mammal. Preferably, the composition that is heated comprises at least 10 percent by weight of diazepam. More preferably, the composition comprises 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of diazepam.

Typically, the delivered aerosol particles comprise at least 5 percent by weight of diazepam. Preferably, the particles comprise at least 10 percent by weight of diazepam. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of diazepam.

Typically, the condensation aerosol has a mass of at least 10 µg. Preferably, the aerosol has a mass of at least 100 µg. More preferably, the aerosol has a mass of at least 200µ.

Typically, the delivered aerosol particles comprise less than 10 percent by weight of diazepam degradation products. Preferably, the particles comprise less than 5 percent by weight of diazepam degradation products. More preferably, the particles comprise less than 2.5, 1, 0.5, 0.1 or 0.03 percent by weight of diazepam degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the delivered aerosol has an inhalable aerosol drug mass density of between 0.1 mg/L and 15 mg/L.

Preferably, the aerosol has an inhalable aerosol drug mass density of between 0.2 mg/L and 10 mg/L. More preferably, the aerosol has an inhalable aerosol drug mass density of between 0.5 mg/L and 8 mg/L.

Typically, the delivered aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered aerosol is formed at a rate greater than 0.25 mg/second. Preferably, the aerosol is formed at a rate greater than 0.5 mg/second. More preferably, the aerosol is formed at a rate greater than 1 or 2 mg/second.

Typically, the condensation aerosol delivers between 0.2 mg and 20 mg of diazepam to the mammal in a single inspiration. Preferably, between 0.35 mg and 10 mg of diazepam are delivered to the mammal in a single inspiration. More preferably, between 0.5 mg and 8 mg of diazepam are delivered to the mammal in a single inspiration.

Typically, the delivered condensation aerosol results in a peak plasma concentration of diazepam in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

Typically, the delivered condensation aerosol is used to treat anxiety.

In a kit aspect of the present invention, a kit for delivering diazepam through an inhalation route to a mammal is provided which comprises: a) a composition comprising at least 5 percent by weight of diazepam; and, b) a device that forms a diazepam containing aerosol from the composition, for inhalation by the mammal. Preferably, the composition comprises at least 10 percent by weight of diazepam. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of diazepam.

Typically, the device contained in the kit comprises: a) an element for heating the diazepam composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
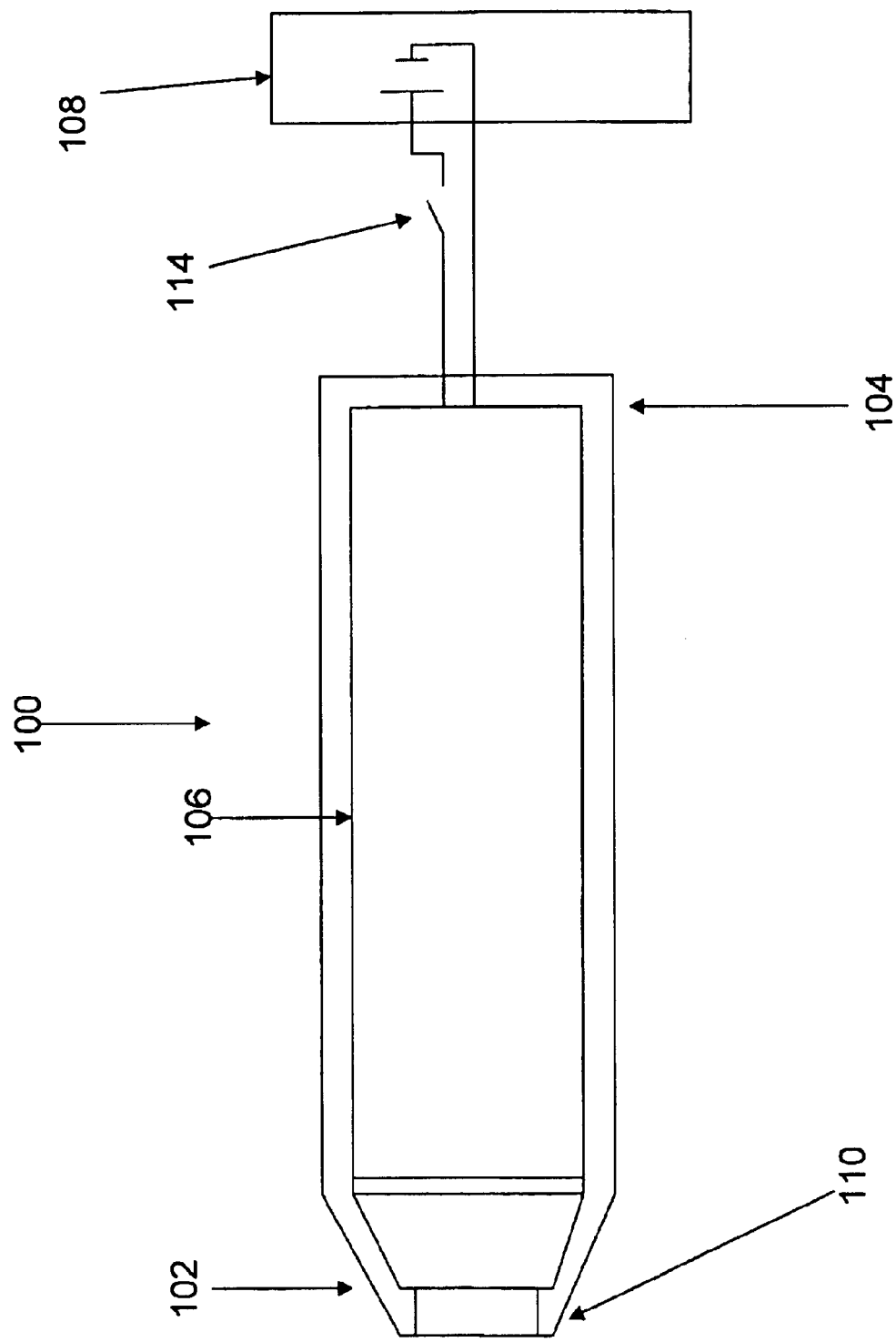
FIG. 1 shows a device used to deliver diazepam containing aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of diazepam per unit volume of aerosol.

"Aerosol mass density" refers to the mass of particulate matter per unit volume of aerosol.

"Aerosol particle density" refers to the number of particles per unit volume of aerosol.

"Condensation aerosol" refers to an aerosol formed by vaporization of a substance followed by condensation of the substance into an aerosol.

"Diazepam" refers to 7-chloro-1,3-dihydro-1-methyl-5-phenyl-2H-1,4-benzodiazepin-2-one.

"Diazepam" degradation product refers to a compound resulting from a chemical modification of diazepam. The modification, for example, can be the result of a thermally or photochemically induced reaction. Such reactions include, without limitation, oxidation and hydrolysis. Examples of products from such reactions include $C_{16}H_{15}N_2O_2Cl$ (imine hydrolysis) and $C_{14}H_{12}NOCl$ (imine hydrolysis followed by amide hydrolysis).

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized diazepam produced by an inhalation device per unit time.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Diazepam Containing Aerosols

Any suitable method is used to form the aerosols of the present invention. A preferred method, however, involves heating a composition comprising diazepam to produce a vapor, followed by cooling of the vapor such that it condenses to provide a diazepam comprising aerosol (condensation aerosol). The composition is heated in one of two forms: as pure active compound (i.e., pure diazepam); or, as a mixture of active compound and a pharmaceutically acceptable excipient. Typically, the composition is heated on a solid support.

Pharmaceutically acceptable excipients are either volatile or nonvolatile. Volatile excipients, when heated, are concurrently volatilized, aerosolized and inhaled with diazepam. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the diazepam compositions is performed using any suitable method. Examples of methods by which heat can be generated include the following: passage of current through an electrical resistance element; absorption of electromagnetic radiation, such as microwave or laser light; and, exothermic chemical reactions, such as exothermic salvation, hydration of pyrophoric materials and oxidation of combustible materials.

Delivery of Diazepam Containing Aerosols

Diazepam containing aerosols of the present invention are delivered to a mammal using an inhalation device. Where the aerosol is a condensation aerosol, the device has at least three elements: an element for heating a diazepam containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver diazepam containing aerosol is described in reference to FIG. 1. Delivery device 100 has a proximal end 102 and a distal end 104, a heating module 106, a power source 108, and a mouthpiece 110. A diazepam composition is deposited on a surface 112 of heating module 106. Upon activation of a user activated switch 114, power source 108 initiates heating of heating module 106 (e.g, through ignition of combustible fuel or passage of current through a resistive heating element). The diazepam composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of diazepam containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Diazepam Containing Aerosols

For the management of anxiety disorders and relief of anxiety symptoms, diazepam is given orally at strengths of 2 mg to 10 mg, 2 to 4 times daily. As an aerosol, 0.2 mg to 20 mg of diazepam is generally provided per inspiration for the same indication. A typical dosage of a diazepam aerosol is either administered as a single inhalation or as a series of inhalations taken within an hour or less. Where the drug is administered as a series of inhalations, a different amount may be delivered in each inhalation.

One can determine the appropriate dose of a diazepam containing aerosol to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Diazepam Containing Aerosols

Purity of a diazepam containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of diazepam degradation products.

Particle size distribution of a diazepam containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles= Sum (from size range 1 to size range N) of number of particles in each size range. Number of particles in a given size range=Mass in the size range/Mass of a typical particle in the size range. Mass of a typical particle in a given size range=$\pi*D^3*\phi/6$, where D is a typical particle diameter in the size range (generally, the mean of the boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering a diazepam containing aerosol into a confined chamber via an inhalation device over a set period of time (e.g., 3 s). Where the aerosol is pure diazepam, the amount of drug collected in the chamber is measured as described above. The rate of drug aerosol formation is equal to the amount of diazepam collected in the chamber divided by the duration of the collection time. Where the diazepam containing aerosol comprises a pharmaceutically acceptable excipient, multiplying the rate of aerosol formation by the percentage of diazepam in the aerosol provides the rate of drug aerosol formation.

Utility of Diazepam Containing Aerosols

The following are, without limitation, typical indications for diazepam aerosols: moderate and severe anxiety disorders and symptoms of anxiety; panic attacks and situational anxiety; acute alcohol withdrawal; muscle spasm; insomnia; and, nausea.

The following examples are meant to illustrate, rather than limit, the present invention.

Diazepam was purchased from Sigma (www.sigma-aldrich.com).

EXAMPLE 1

Volatilization of Diazepam

Diazepam (10.0 mg) in 120 µL dichloromethane was coated onto a circular piece of aluminum foil (10 cm in diameter). The dichloromethane was allowed to evaporate. Assuming a drug density of about 1 g/cc, the calculated thickness of the diazepam coating on the 78.5 cm² aluminum solid support, after solvent evaporation, is about 1.3 microns. The aluminum foil was secured onto a 100 mm×50 mm petridish using parafilm. After cooling the glass bottom of the petridish with dry ice, the aluminum side of the apparatus was placed on a hot plate at 240° C. for 10 s. The apparatus was removed from the hot plate and allowed to cool. Acetonitrile was injected through the aluminum foil onto the inside of the glass surface using a 3 mL syringe. The acetonitrile solution was concentrated and analyzed by high performance liquid chromatography with UV absorbance detection at 225 nm light, which indicated that the volatilized material was at least 99.9% pure.

EXAMPLE 2

Volatilization of Diazepam Using a Halogen Bulb Heat Source

A solution of 5.3 mg diazepam in 120 µL dichloromethane was coated on a 3 cm×8 cm piece of aluminum foil. The dichloromethane was allowed to evaporate. Assuming a drug density of about 1 g/cc, the calculated thickness of the diazepam coating on the 24 cm² aluminum solid support, after solvent evaporation, is about 2.2 microns. The coated foil was wrapped around a 300 watt halogen tube (Feit Electric Company, Pico Rivera, Calif.), which was inserted into a glass tube sealed at one end with a rubber stopper. Running 40 V of alternating current (driven by line power controlled by a variac) through the bulb for 17 s afforded diazepam thermal vapor (including diazepam aerosol), which collected on the glass tube walls. Reverse-phase HPLC analysis with detection by absorption of 225 nm light showed the collected material to be at least 99.9% pure diazepam.

EXAMPLE 3

Particle Size, Particle Density, and Rate of Inhalable Particle Formation of Diazepam Aerosol A solution of 18.2 mg diazepam in 200 μL dichloromethane was spread out in a thin layer on the central portion of a 4 cm×9 cm sheet of aluminum foil. The dichloromethane was allowed to evaporate. Assuming a drug density of about 1 g/cc, the calculated thickness of the diazepam thin layer on the 36 cm² aluminum solid support, after solvent evaporation, is about 5.1 microns. The aluminum foil was wrapped around a 300 watt halogen tube, which was inserted into a T-shaped glass tube. One of the openings of the tube was sealed with a rubber stopper, another was loosely covered with the end of the halogen tube, and the third was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 1.74 microns with a geometric standard deviation of 2.02. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm³). The inhalable aerosol particle density is the sum of the numbers of particles collected on impactor stages 3 to 8 divided by the collection volume of 1 L, giving an inhalable aerosol particle density of $5.87 \times 10^{10}$ particles/L ($5.87 \times 10^7$ particles/mL). The rate of inhalable aerosol particle formation is the sum of the numbers of particles collected on impactor stages 3 through 8 divided by the formation time of 6 s, giving a rate of inhalable aerosol particle formation of $9.8 \times 10^9$ particles/second.

TABLE 1

Determination of the characteristics of a diazepam condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.2 | $4.46 \times 10^5$ |
| 1 | 5.8–9.0 | 7.4 | 0 | 0 |
| 2 | 4.7–5.8 | 5.25 | 0.3 | $3.96 \times 10^6$ |
| 3 | 3.3–4.7 | 4.0 | 0.8 | $2.39 \times 10^7$ |
| 4 | 2.1–3.3 | 2.7 | 1.4 | $1.36 \times 10^8$ |
| 5 | 1.1–2.1 | 1.6 | 2.8 | $1.31 \times 10^9$ |
| 6 | 0.7–1.1 | 0.9 | 1.3 | $3.41 \times 10^9$ |
| 7 | 0.4–0.7 | 0.55 | 0.4 | $6.11 \times 10^9$ |
| 8 | 0–0.4 | 0.2 | 0.2 | $4.77 \times 10^{10}$ |

EXAMPLE 4

Drug Mass Density and Rate of Drug Aerosol Formation of Diazepam Aerosol

A solution of 5.1 mg diazepam in 200 μL dichloromethane was spread out in a thin layer on the central portion of a 4 cm×9 cm sheet of aluminum foil. The dichloromethane was allowed to evaporate. Assuming a drug density of about 1 g/cc, the calculated thickness of the diazepam coating on the 36 cm² aluminum solid support, after solvent evaporation, is about 2.2 microns. The aluminum foil was wrapped around a 300 watt halogen tube, which was inserted into a T-shaped glass tube. One of the openings of the tube was sealed with a rubber stopper, another was loosely covered with the end of the halogen tube, and the third was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with dichloromethane and the extract analyzed by HPLC with detection by light absorption at 225 nm. Comparison with standards containing known amounts of diazepam revealed that 3.8 mg of >99% pure diazepam had been collected in the flask, resulting in an aerosol drug mass density of 3.8 mg/L. The aluminum foil upon which the diazepam had previously been coated was weighed following the experiment. Of the 5.1 mg originally coated on the aluminum, all of the material was found to have aerosolized in the 6 s time period, implying a rate of drug aerosol formation of 0.85 mg/s.

What is claimed is:

1. A composition for delivery of diazepam comprising a condensation aerosol a) formed by volatilizing the diazepam under conditions effective to produce a heated vapor of the diazepam and condensing the heated vapor of the diazepam to form condensation aerosol particles, b) wherein said condensation aerosol particles are characterized by less than 5% diazepam degradation products, and c) wherein the aerosol MMAD is less than 3 microns.

2. The composition according to claim 1, wherein the condensation aerosol has a mass of at least 0.10 mg.

3. The composition according to claim 1, wherein the condensation aerosol particles comprise less than 2.5 percent by weight of diazepam degradation products.

4. The composition according to claim 1, wherein the condensation aerosol particles comprise at least 90 percent by weight of diazepam.

5. The composition according to claim 4, wherein the condensation aerosol has a mass median aerodynamic diameter less than 2 microns.

6. The composition according to claim 5, wherein the condensation aerosol particles comprise at least 97 percent by weight of diazepam.

7. A method of producing diazepam in an aerosol form comprising:
   a) volatilizing diazepam under conditions effective to produce a heated vapor of the drug, and
   b) during said volatilizing, passing air through the heated vapor to produce aerosol particles of the diazepam comprising less than 5% diazepam degradation products and an aerosol having an MMAD less than 3 $\mu$m.

8. The method according to claim 7, wherein said volatilizing includes heating a thin layer which includes the diazepam and which is on a solid support having the surface texture of a metal foil, to a temperature sufficient to volatilize the diazepam from the thin layer.

9. The method according to claim 7, wherein the aerosol has a mass of at least 0.10 mg.

10. The method according to claim 7, wherein the aerosol particles are formed at a rate of greater than 0.85 mg/sec.

11. The method according to claim 7, wherein the aerosol particles comprise less than 2.5 percent by weight of diazepam degradation products.

12. The method according to claim 7, wherein the aerosol particles comprise at least 90 percent by weight of diazepam.

13. The method according to claim 12, wherein the aerosol has a mass median aerodynamic diameter less than 2 microns.

14. The method according to claim 13, wherein the aerosol particles comprise at least 97 percent by weight of diazepam.

15. The method according to claim 8, wherein the thin layer which includes diazepam on said solid support surface has a thickness between 1.3 and 5.1 microns.

* * * * *